United States Patent

Hack

[11] Patent Number: 6,146,376
[45] Date of Patent: Nov. 14, 2000

[54] PULSED LIGHT SOURCE

[75] Inventor: Alexander Hack, Biberach, Germany

[73] Assignee: Kaltenbach & Voight GmbH & co., Biberach, Germany

[21] Appl. No.: 09/099,696

[22] Filed: Jun. 18, 1998

[30] Foreign Application Priority Data

Jul. 23, 1997 [DE] Germany .............................. 197 31 699

[51] Int. Cl.[7] .................................................. A61N 5/06
[52] U.S. Cl. .................................. 606/13; 606/10; 606/2
[58] Field of Search ................................ 606/2, 3, 10, 11, 606/12, 14, 15, 16, 17

[56] References Cited

U.S. PATENT DOCUMENTS

| | | | |
|---|---|---|---|
| 4,791,927 | 12/1988 | Menger | 606/10 |
| 5,387,211 | 2/1995 | Saadatmanesh et al. | 606/12 |
| 5,531,738 | 7/1996 | Hessel et al. | 606/2 |
| 5,540,676 | 7/1996 | Freiberg | 606/3 |
| 5,662,644 | 9/1997 | Swor | 606/9 |
| 5,717,806 | 2/1998 | Pileski et al. | 606/16 |
| 5,746,735 | 5/1998 | Furumoto et al. | 606/9 |
| 5,785,702 | 7/1998 | Murphy-Chutorian | 606/7 |
| 5,832,013 | 11/1998 | Yessik et al. | 372/26 |
| 5,873,875 | 2/1999 | Altshuler | 606/10 |

FOREIGN PATENT DOCUMENTS

| | | |
|---|---|---|
| 38 33 993 A1 | 4/1990 | Germany . |
| 40 30 240 A1 | 2/1991 | Germany . |
| 38 33 992 C2 | 3/1992 | Germany . |
| 92 08 617 U | 10/1992 | Germany . |
| 38 33 990 C2 | 5/1995 | Germany . |
| 44 39 763 A1 | 5/1996 | Germany . |
| 195 21 003 C1 | 8/1996 | Germany . |
| 295 05 195 U1 | 9/1996 | Germany . |
| 43 41 967 C2 | 1/1997 | Germany . |
| WO 93/21843 | 11/1993 | WIPO . |

*Primary Examiner*—Linda C. M. Dvorak
*Assistant Examiner*—Sonya Harris Ogugua
*Attorney, Agent, or Firm*—Marshall, O'Toole, Gerstein, Murray & Borun

[57] ABSTRACT

Pulsed light source for the removal of biological tissue. The pulsed light source incorporates light means as well as a controller which controls the light means in such a way that the light means generate on the one hand ablation pulses (BA) with an irradiancy sufficient for the ablation of tissue and on the other hand a coagulation radiation (BK) with an irradiance sufficient simply for a heating of tissue, but not for an ablation of tissue. The controller controls the light means in such a way that the light means generate the coagulation radiation (BK) independently in time of the ablation pulses (BA).

18 Claims, 5 Drawing Sheets

PULSED LIGHT SOURCE

BACKGROUND OF THE INVENTION

1. Technical Field

The present invention relates to a pulsed light source for the removal of biological tissue with light means and a controller for controlling the light means in such a way that the light means generate on the one hand ablation pulses with a particular pulse frequency and an irradiance sufficient for ablation of tissue and on the other hand a coagulation radiation with an irradiance which is certainly sufficient for a heating of tissue, but not for an ablation of tissue. In particular the present invention relates to a pulsed light source of the kind described above for use in the dental field.

2. Background Information

As is known, biological tissue can be removed with the aid of high-energy light radiation, for example with laser radiation. The surrounding tissue is heated, however, if a sufficiently intensive light is used, the degree of said heating being dependent in particular both on the wavelength of the radiation used and the absorption coefficient of the tissue, said absorption coefficient being dependent on said wavelength, and on the irradiance. On the removal or cutting of biological tissue the depression thereby caused or the cut is surrounded by a carbonisation zone, a zone loosened by vacuoles, a coagulation zone and a reversibly thermally damaged area. In order to achieve as good a wound-healing process as possible and as little damage to the tissue as possible, the smallest thermal effects as possible are advantageous. The formation of a carbonisation layer, i.e. the carbonisation of the tissue surface, such as occurs with cutting with continuous wave lasers, is undesirable. The coagulation zone produced by the heating and the associated hemostasis is advantageous, however, if the capillary layer is damaged during the treatment of the tissue, since otherwise the escaping blood would affect the removal of the tissue. The coagulation zone produced by the heating therefore makes non-bleeding cuts possible.

It is known that tissue can be removed with pulsed light sources of high output and a wavelength in the ultraviolet or infrared range without carbonisation of the tissue surface and with relatively little thermal damage. A relatively small coagulation zone is moreover formed, which has for example a thickness of only 30–40 $\mu$m. A small coagulation zone of this kind is advantageous in particular for the treatment of superficial skin lesions and for cosmetic surgery, since damage to the tissue which goes beyond the removal of the tissue is avoided. As has already been described before, however, it is not possible with such a small coagulation zone, if the capillary layer is affected, for a non-bleeding cut to be obtained, since the escaping blood then affects the removal of the tissue and in certain cases even impedes it.

There was therefore a requirement for a light source for the removal of biological tissue, by means of which on the one hand tissue can be removed as precisely as possible and with as few thermal side-effects as possible and without carbonisation of the tissue surface and on the other a coagulation zone specific to the respective application can be produced and formed. To this end a pulsed light source was proposed in DE-C1-195 21 003 according to the preamble of claim 1. Said pulsed light source comprises a controller which controls the light source in such a way that the light source generates with a predetermined pulse frequency short ablation pulses for the ablation, i.e. for the removal, of the tissue, wherein each ablation pulse is followed by a coagulation irradiation whose irradiance does not suffice for the removal of tissue, but leads to a heating of the tissue, which in turn supports the formation of a coagulation zone. The generation of the ablation pulses therefore makes it possible to achieve on the one hand, without formation of a carbonisation layer, a very effective thermo-mechanical ablation process with relatively little thermal damage to the remaining tissue. This is of particular interest in particular for the treatment of superficial skin lesions or for cosmetic surgery. On the other hand there is promoted with the artificial heating of the tissue which results from the coagulation irradiation following each ablation pulse the formation of a coagulation zone, wherein the associated hemostasis makes non-bleeding cuts possible even if the capillary layer of the tissue is damaged, i.e. even if the capillary layer of the tissue is damaged the ablation is not affected by escaping blood.

According to DE-C1-195 21 003 each ablation pulse is always followed by a coagulation radiation, wherein the coagulation radiation can likewise be realised in the form of pulses. The generation of the coagulation radiation is however dependent in each case on the generation of a preceding ablation pulse. This makes the control of the pulsed light source by the controller labourious.

SUMMARY OF THE INVENTION

The present invention is therefore based on the aim of developing a pulsed light source of the kind described beforehand in such a way that the control of the light source by the controller is facilitated.

In particular it is also to be possible with the pulsed light source of the present invention on the one hand for biological tissue to be removed as precisely as possible and with as few thermal side-effects as possible and without carbonisation of the tissue surface and on the other for the tissue to be heatable deliberately and controllably for the formation of a coagulation zone specific to the application.

The above-mentioned aim is achieved according to the present invention by a pulsed light source for the removal of biological tissue, with light means and with a controller for controlling the light means in such a way that the light means generate on the one hand ablation pulses (BA) with a particular pulse frequency and an irradiance sufficient for the ablation of tissue and on the other hand a coagulation radiation (BK) with an irradiance which is certainly sufficient for a heating of tissue, but not for an ablation of tissue, wherein the controller in addition controls the light means in such a way that the light means generate the coagulation radiation(BK)independently of the ablation pulses (BA).

The pulsed light source according to the invention generates, like the pulsed light source known from DE-C1-195 21 003, ablation pulses with a particular pulse frequency and an irradiance sufficient for the ablation, i.e. for the removal, of tissue. Furthermore a coagulation radiation is generated which leads simply to a heating of the tissue, but whose irradiance does not however suffice for the ablation of tissue. According to the present invention, however, in contrast to DE-C1-195 21 003, the generation of the coagulation radiation is not tied to the occurrence of a preceding ablation pulse. The coagulation radiation is rather generated independently of the ablation pulses. The operation of the controller for controlling the pulsed light source is facilitated in this way, wherein however the advantages of the pulsed light source known from DE-C1-195 21 003 are still retained. This means that it is possible, by the generation of ablation pulses with an irradiance sufficient for the ablation of biological tissue, to achieve without carbonisation a very effective thermo-mechanical ablation process with relatively little thermal damage to the remaining tissue. This is of advantage in particular for the treatment of superficial skin lesions and for cosmetic surgery. By the generation of a coagulation radiation which does not have sufficient irradiance for an ablation of tissue, the tissue can be heated artificially, so that the formation of a coagulation zone is supported. This means that even if the capillary layer of the tissue is affected by the hemostasis associated with the coagulation, an impairment by escaping blood of the tissue removal or of the tissue cut is prevented. The thermal side-effect, as well as the associated thickness of the coagulation zone, can be adjusted to the individual surgical procedure, so that a thermal necrosis zone which is just sufficient and hence does minimum damage can be produced in each case. The artificially enlarged coagulation zone moreover does not interfere with the quality of the cut, so that non-bleeding cuts of the greatest possible precision can be achieved in each case with the aid of the pulsed light source according to the invention.

The ablation pulses as well as the coagulation radiation can be generated both by one and the same light means and by two separate light means. According to a preferred embodiment, however, the pulsed light source comprises only one light means, such as e.g. an Er:YAG laser with a wavelength in the infrared range, which is activated by the controller of the pulsed light source in such a way that the light means generates both the ablation pulses and the coagulation radiation. Other conventional pulsed laser types can also be used as light means, such as e.g. Ho:YAG, CO2, Er:YSGG, Tm:YAG, CO or Excimer lasers. There is the additional possibility, instead of the use of pulsed lasers, of also using pulsed high-pressure gas-discharge lamps, laser diodes or other flash lamps.

According to a first embodiment of the present invention the coagulation radiation is generated continuously, so that the ablation pulses are superimposed on the coagulation radiation. This embodiment can be realised particularly easily with a single pulsed light means which generates the coagulation radiation permanently and on the other hands emits the ablation radiation for the removal of the biological tissue after the manner of a pulse. The coagulation radiation can in so doing exhibit an irradiance constant over time. In order to prevent a disproportionate heating of the tissue, the coagulation radiation can however also exhibit an irradiance varying in time. This development also makes sense in view of the fact that with increasing radiation and increasing enlargement of the cut of the tissue to be treated the threshold value of the irradiance, at which ablation of the tissue still does not quite occur, decreases. This fact can be allowed for with an irradiance of the coagulation radiation which decreases over time. In addition it is also possible to generate a coagulation radiation with an irradiance varying after the manner of a wave, sine, zigzag or saw-tooth etc.

According to a second embodiment of the present invention the coagulation radiation is also generated in the form of pulses together with the ablation radiation. The coagulation pulses, however, always possess an irradiance which suffices simply for the heating of the tissue, but cannot lead to an ablation of the tissue. Said coagulation pulses are super-imposed on the ablation pulses serving for the removal of biological tissue. Since the coagulation radiation or the coagulation pulses are generated independently of the occurrence of the ablation pulses, a phase shift between the coagulation pulses and the ablation pulses can occur. Likewise the case can occur where an ablation pulse is generated at least in part simultaneously with a coagulation pulse. The coagulation pulses can exhibit an identical irradiance and an identical pulse width. It is likewise also possible, however, that only the energy content of one and every coagulation pulse is kept constant, so that in this case the coagulation pulses can exhibit different irradiancies and different pulse widths, wherein however the product of irradiance and pulse width is constant.

In order to achieve a best possible adaptation of the treatment to the particular tissue to be treated, the radiation parameters both of the ablation pulses and of the coagulation radiation can with advantage be adapted to the particular application and set. The pulse width, the pulse frequency and the irradiance of the ablation pulses can be set in this way. In addition the irradiance, and in the case of a pulse-type coagulation radiation also the pulse width and the pulse frequency of the coagulation radiation, can be set, in order to be able to form a coagulation zone specific to the particular intended use, i.e. a thermal necrosis zone which is just sufficient and thus does minimum damage.

The present invention will now be described by way of example only, with reference to the accompanying drawings in which:

DESCRIPTION OF THE PREFERRED EMBODIMENT

Figure 1:
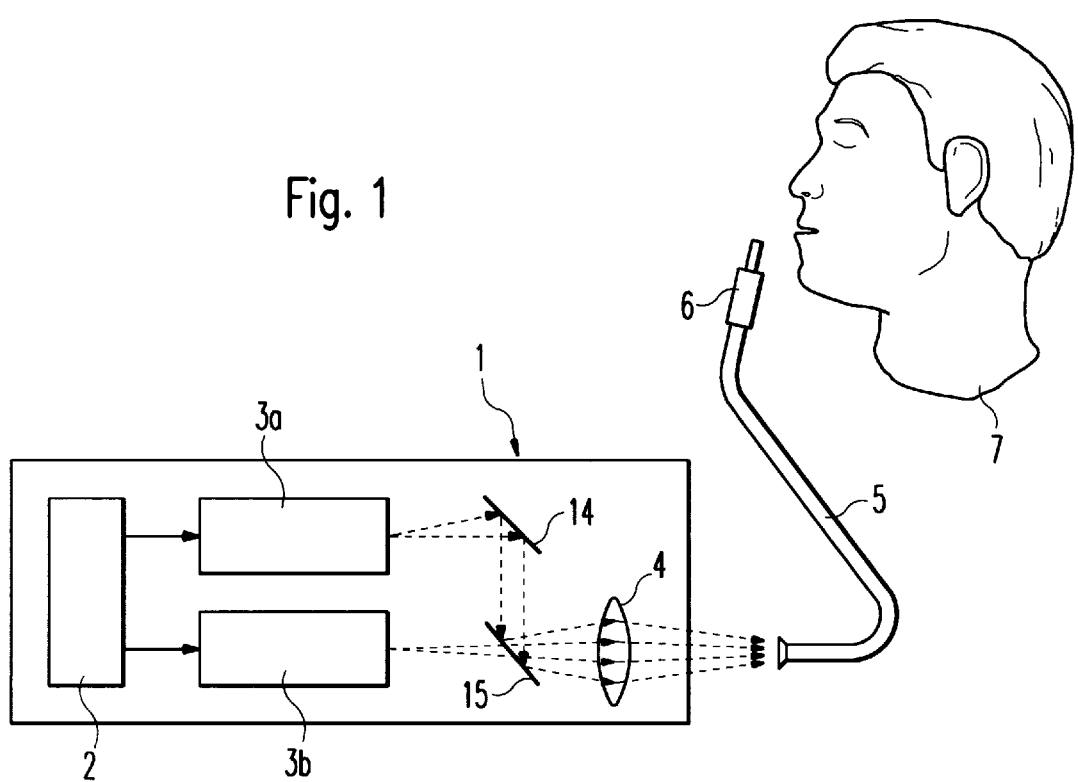
FIG. 1 shows a first variant of the internal composition of a pulsed light source according to the invention.

FIG. 1 shows the possible composition of a pulsed light source 1 according to the invention. The pulsed light source 1 here incorporates a controller 2, two separate light means 3a and 3b as well as an optical system consisting of two deflecting mirrors 14, 15 and a lens arrangement 4. The controller 2 controls the light means 3a and 3b in such a way that the light means 3a generates ablation pulses with a predetermined pulse frequency as well as a predetermined pulse width and irradiance and the light means 3b generates a coagulation radiation with a predetermined irradiance. The irradiance of the ablation pulses is here of sufficient strength to achieve a removal of biological tissue. The irradiance of the coagulation radiation is conversely not sufficient for the removal of tissue. There is achieved with the coagulation radiation simply a heating of the tissue in order to produce the formation of a coagulation zone. The ablation radiation of the light means 3a and the coagulation radiation of the light means 3b are combined via the deflecting mirrors 14 and 15 and coupled with the aid of the lens arrangement 4 into a light guide 5, at whose other end a hand piece 6 with a light probe is disposed. The light guide 5 can comprise several individual light-conducting fibres. It is possible with the hand piece 6 and the light probe affixed thereto to direct the light supplied by the pulsed light source 1 onto the tissue of a patient 7 in order to treat the tissue.

Figure 2:
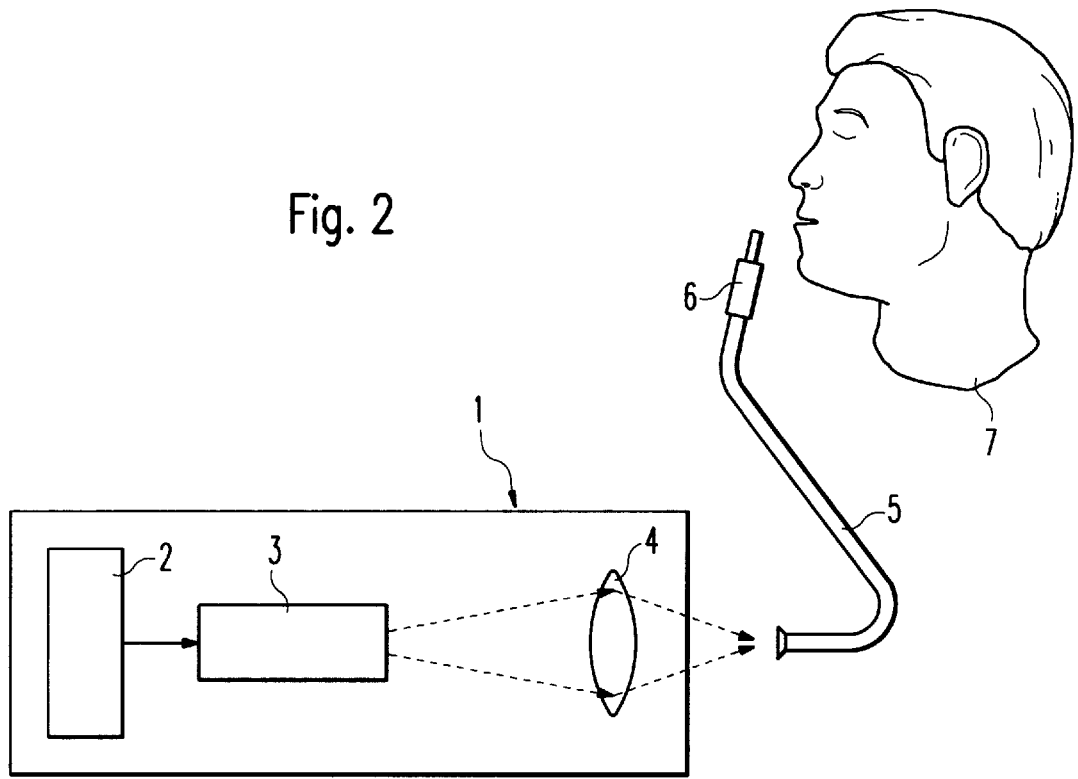
FIG. 2 shows a second variant of the internal composition of a pulsed light source according to the invention.

FIG. 2 shows a preferred variant of the pulsed light source 1 shown in FIG. 1. There is provided here, instead of two separate light means 3a and 3b, only one pulsed light means 3, which generates both the ablation pulses and the coagulation radiation described above. The rest of the composition of the light source 1 corresponds to the composition shown in FIG. 1. The internal composition of the pulsed light source 1 is simplified in this way.

FIG. 3 shows by way of example possible time plots of the ablation radiation BA, the coagulation radiation BK and the total radiation BG resulting therefrom according to a first embodiment of the present invention.

Figure 3A:
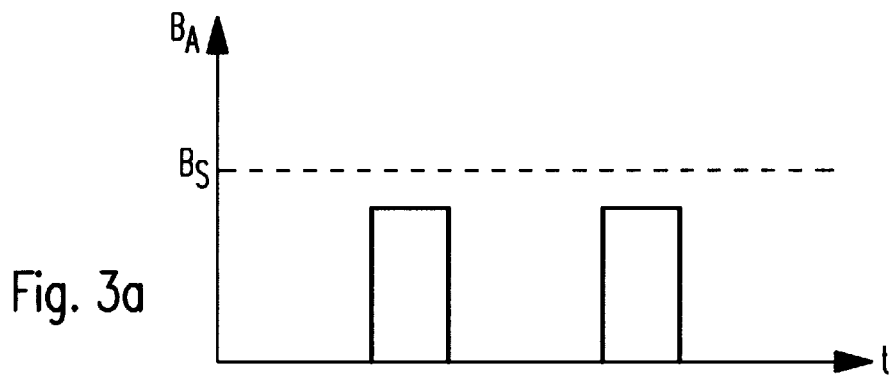
FIGS. 3a–3c show plots of the ablation radiation and of the coagulation radiation according to a first embodiment of the present invention, FIGS. 4a, b
Figure 3B:
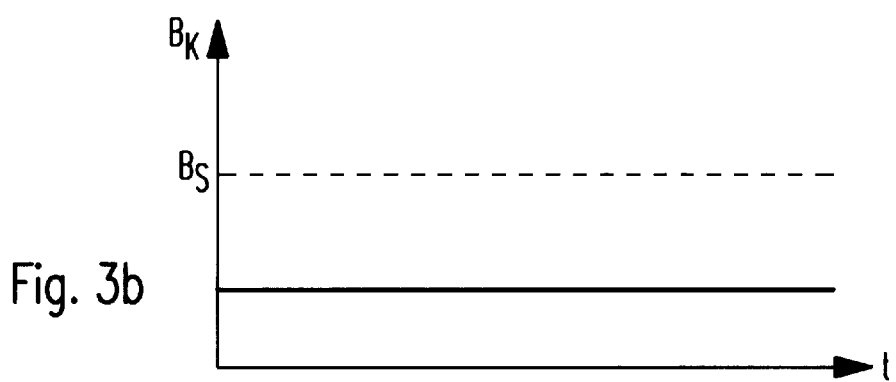
Figure 3C:
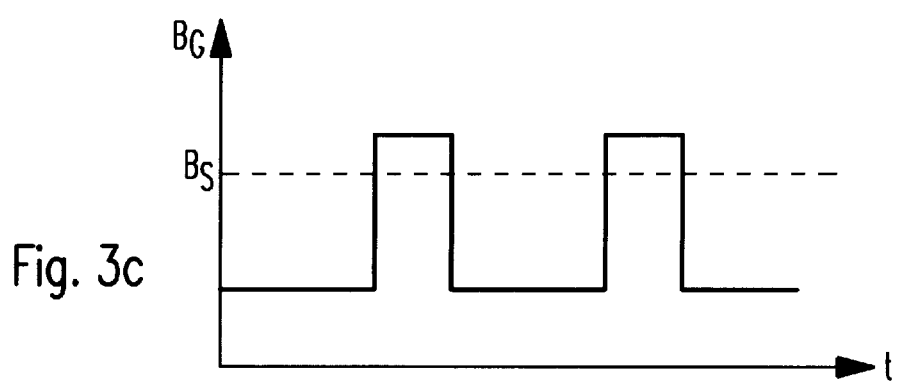

FIG. 3a shows here a pulse-type plot of the ablation radiation, while FIG. 3b represents the continuous generation of a coagulation radiation BK. As can be seen from FIG. 3b, the irradiance of the coagulation radiation is not of sufficient strength to produce an ablation of the tissue occurring from a threshold degree Bs onwards. The superimposition of the ablation radiation BA shown in FIG. 3a with the coagulation radiation shown in FIG. 3b leads to the plot of the total radiation BG shown in FIG. 3c, wherein it can be seen from FIG. 3c that the ablation pulses resulting from the superimposition of the ablation radiation BA and the continuous and constant coagulation radiation BK now exhibit an irradiance which exceed (sic) the threshold value Bs, so that the ablation pulses can be used for the removal of biological tissue. With the embodiment shown in FIG. 3 it is critical that only the ablation pulses produced by the addition of the ablation radiation BA and the coagulation radiation BK exceed the ablation threshold value Bs. This means that optionally—as is shown in FIG. 3a—the irradiance of the actual ablation radiation BA can by virtue of the following superimposition with the coagulation radiation BK lie below the ablation threshold value Bs. As a rule, however, the ablation radiation shown in FIG. 3a will already exceed the ablation threshold value Bs.

As is set out in detail in DE-C1-195 21 003, a tissue ablation, i.e. a tissue removal, occurs if there has accumulated on the tissue surface a particular energy per element of volume, said energy being dependent on the tissue type and on the irradiance. In addition to said energy per element of volume, the ablation threshold value Bs accordingly also depends on the absorption coefficient as well as on the thermal relaxation time of the tissue to be treated and the irradiance. For an Er:YAG laser an ablation threshold value Bs of 1 Jcm-2 can for example be assumed. The ablation pulses shown in FIG. 3c must accordingly exhibit an irradiance BG>1 Jcm-2. For the ablation pulses shown in FIG. 3c the following irradiation parameter ranges are for example possible: irradiance=1–250 Jcm-2, pulse frequency=1–30 Hz, pulse width=100–800 μs. For the case where the ablation pulses and the coagulation radiation are generated with separate light means (cf. FIG. 1), a pulsed light source with a pulse output of>500 W can be used for the generation of the ablation pulses.

The irradiance of the coagulation radiation BK lies significantly below the ablation threshold value Bs and causes simply a heating of the treated tissue. For the case where—as is shown in FIG. 1—the ablation pulses as well as the coagulation radiation are generated by two separate light means, a light source with a light output for example in the range between 0.25 and 10 W can be used to generate the coagulation radiation BK.

As can be seen from FIG. 3, it also holds for the case where the ablation pulses and the coagulation radiation are generated by one and the same light means (cf. FIG. 2) that the coagulation radiation BK is always generated independently of the actual ablation pulses BA, i.e. the occurrence of the coagulation radiation BK is not dependent on the occurrence of an ablation pulse. According to the first embodiment of the present invention the coagulation radiation BK is generated permanently, wherein the irradiance of the coagulation radiation BK is constant in time in accordance with FIG. 3.

In contrast to the time plot of the coagulation radiation BK shown in FIG. 3, however, a plot varying over time of the irradiance of the coagulation radiation BK is also possible. The ablation threshold value Bs decreases with increasing enlargement of the treatment site or of the heated area of the treated tissue. It can therefore make sense to have, for example, a coagulation radiation BK with steadily diminishing irradiance, in order to ensure always that the irradiance of the coagulation radiation does not exceed the ablation threshold value Bs. Care has to be taken here, however, that the coagulation radiation heats the tissue at each point in time in such a way that a coagulation zone of sufficient size can still be formed.

Figure 7:
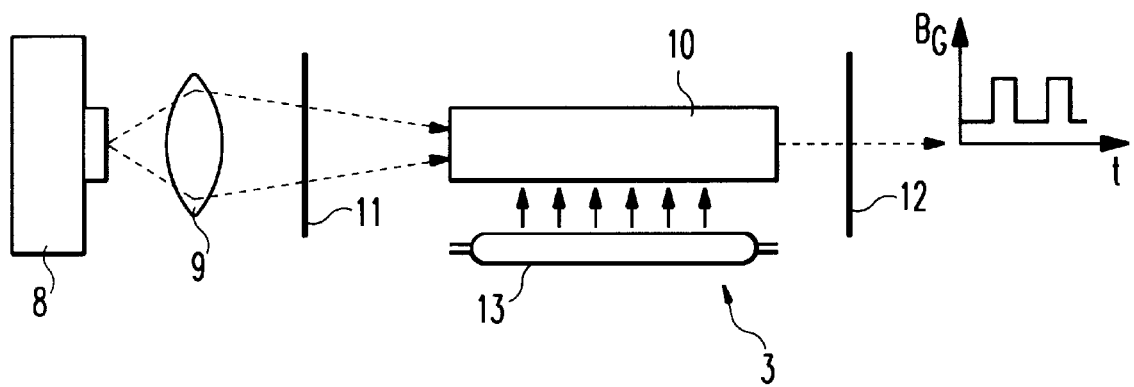
FIG. 7 shows a possible realisation of the variant shown in FIG. 2, in which the coagulation radiation is generated in conformity with FIG. 3.

FIG. 7 shows a possible realisation of the coagulation radiation with superimposed ablation pulses shown in FIG. 3, wherein in accordance with the variant shown in FIG. 2 only one light means is used to generate both the coagulation radiation and the ablation radiation.

There is further used as a light means according to FIG. 7 an Er:YAG laser crystal rod 10, which in order to generate the coagulation radiation (cf. FIG. 3b) is excited continuously by an axially exciting laser diode arrangement 8, wherein the exciting radiation of the laser diode arrangement is supplied to the Er:YAG laser crystal rod 10 via a collimator-lens arrangement 9. The Er:YAG laser rod 10 is in known manner arranged between two resonator mirrors 11 and 12, in order in this way to achieve an optical resonance. At the same time the Er:YAG laser rod 10 is operated in pulsed mode by a flash lamp 13, whereby the ablation pulses are generated, which are superimposed on the coagulation radiation and finally outputted as modulated total radiation BG by the light means 3 (cf. FIG. 3a and 3c).

Figure 4A:
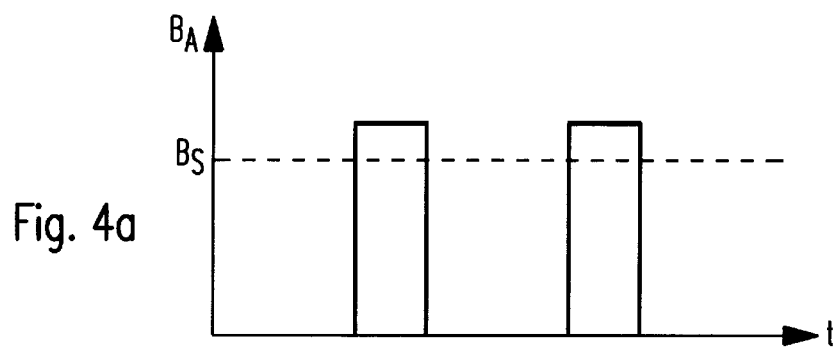
Figure 4B:
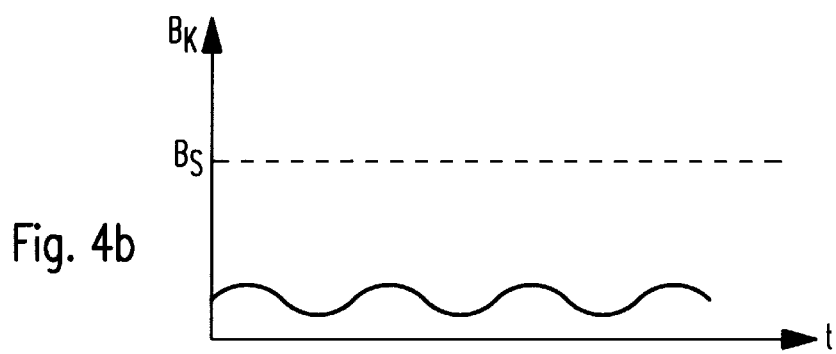
Figure 5A:
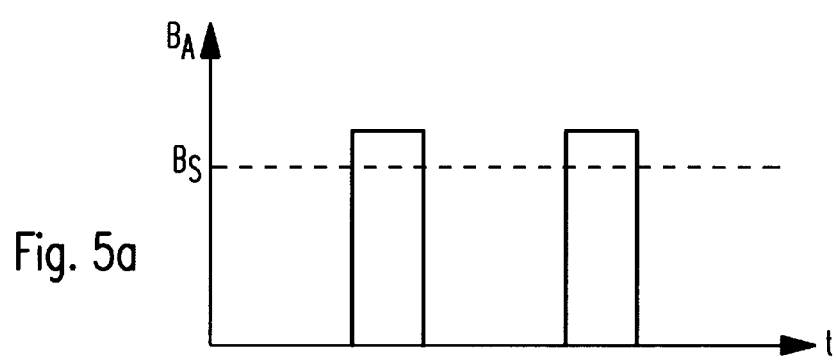
FIGS. 5a, 5b show variants of the first embodiment shown in FIG. 3 and FIGS. 6a–6c show plots of the ablation radiation and of the coagulation radiation according to a second embodiment of the present invention
Figure 5B:
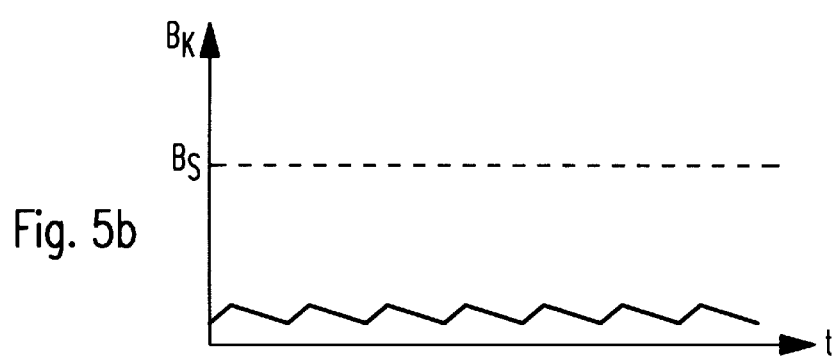

As is shown in FIGS. 4 and 5, the irradiance BK can also vary periodically over time. There is possible for example according to FIG. 4b a sine- or wave-type plot of the irradiance of the coagulation radiation BK, in order to prevent a disproportionately strong heating of the treated tissue. According to FIG. 5b the plot of the coagulation radiation BK can also be provided with a zigzag- or sawtooth-type shape. A disproportionate heating of the treated tissue site by the coagulation radiation is prevented in this way. As follows from FIG. 4a and FIG. 5a, the respective pulses shown exceed the ablation threshold value Bs. It has already been explained from FIG. 3, however, that it is sufficient in principle if the ablation pulses resulting from the superimposition of the pulses BA with the coagulation radiation BK exceed the ablation threshold value Bs.

Figure 6A:
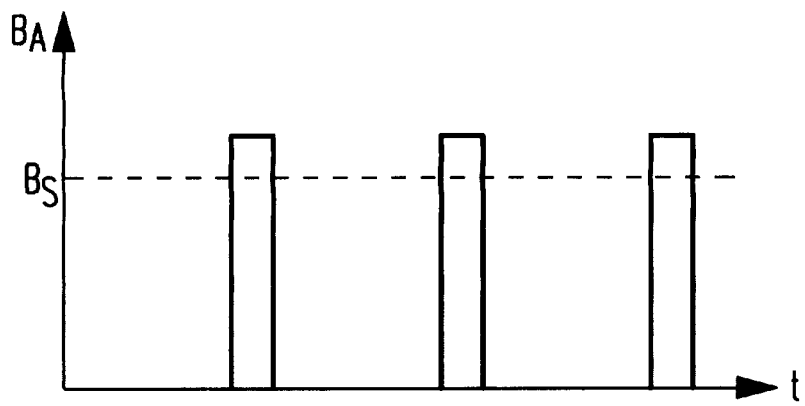
Figure 6B:
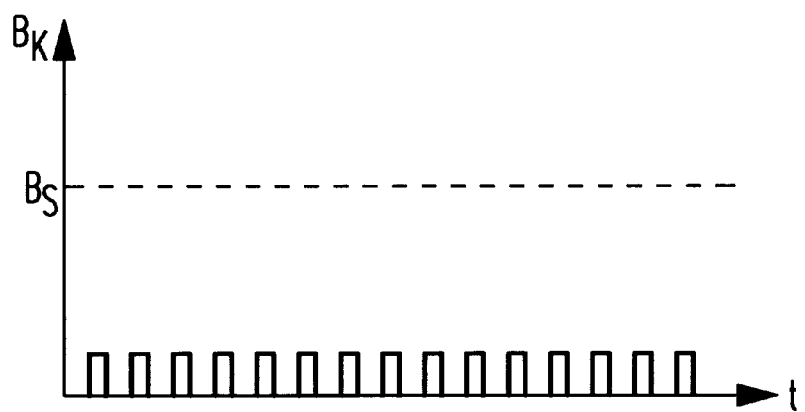
Figure 6C:
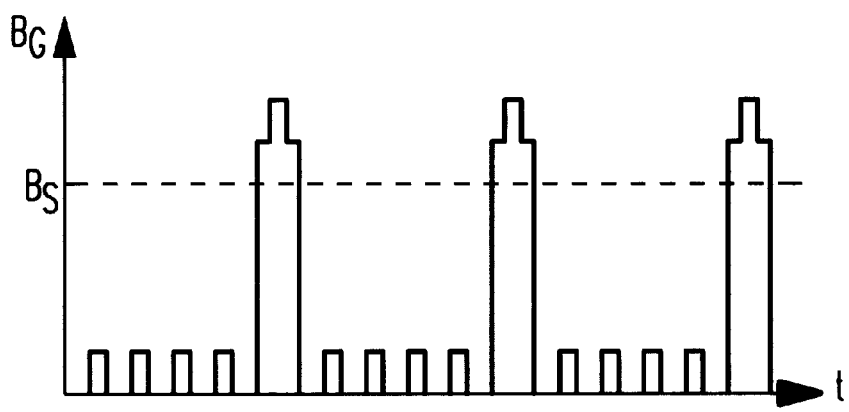

A second embodiment of the control of the pulsed light source according to the invention will now be explained from FIG. 6. FIG. 6a shows in turn here the pulse-type ablation radiation BA. In contrast to the coagulation radiation explained from FIGS. 3–5, according to FIG. 6 the coagulation radiation is generated not continuously, but after the manner of a pulse. The coagulation radiation BK therefore exhibits the time plot shown in FIG. 6b, wherein the irradiance of the individual coagulation pulses lies significantly below the ablation threshold value Bs. FIG. 6c shows a plot of the total radiation, which is obtained by the superimposition of the ablation radiation BA with the coagulation radiation BK. Since the coagulation pulses overlap in some cases the ablation pulses, there is obtained in certain places—as can be seen in FIG. 6—a vertical exaggeration of the ablation pulses. In the embodiment shown in FIG. 6 it suffices if the energy content of each coagulation pulse lies below the ablation threshold value. This means that in principle the individual coagulation pulses can also exhibit different irradiancies and pulse widths, wherein only the product of the irradiance and the pulse width of each and every coagulation pulse must lie below the corresponding ablation threshold value. The frequency of the coagulation pulses is significantly higher than that of the ablation pulses and can lie for example in the vicinity of 100 Hz. Similarly the pulse width of the coagulation pulses is significantly smaller than that of the ablation pulses and can lie for example in the vicinity of 10 $\mu$s. In order to be able to adjust the heat generation and hence the thickness of the coagulation zone resulting from the coagulation radiation to individual requirements, the irradiance, the pulse width and the pulse frequency of the coagulation pulses can be set user-specifically.

In the case also of the embodiment shown in FIG. 6 the coagulation radiation, i.e. the coagulation pulses, is always generated independently of the ablation pulses, i.e. the occurrence of the coagulation pulses is not tied to a preceding occurrence of an ablation pulse, but rather the coagulation pulses are generated continuously. The control of the pulsed light source according to the invention can be simplified in this way.

What is claimed is:

1. A pulsed light source for the removal of biological tissue, with light means including a single, common light source and a controller for controlling the light source in such a way that the light source generates on the one hand ablation pulses with a particular pulse frequency and an irradiance sufficient for the ablation of tissue and on the other hand a coagulation radiation with an irradiance which is certainly sufficient for a heating of tissue, but not for an ablation of tissue, wherein the controller in addition controls the light source in such a way that the light source generates the coagulation radiation as a substantially continuous waveform and the ablation pulses as a pulsed waveform superimposed on the substantially continuous waveform.

2. A pulsed light source as claimed in claim 1, wherein the irradiance of the ablation pulses lies in the range 1–250 Jcm-2.

3. A pulsed light source as claimed in claim 2, wherein at least one of the irradiance, the pulse width and pulse frequency of the ablation pulses is settable.

4. A pulsed light source as claimed in claim 1, wherein the pulse width of the ablation pulses is in the range 100–800 $\mu$s.

5. A pulsed light source as claimed in claim 1, wherein the pulse frequency of the ablation pulses lies in the range 1–30 Hz.

6. A pulsed light source as claimed in claim 1, wherein the irradiance of the coagulation radiation is smaller than 1 Jcm-2.

7. A pulsed light source as claimed in claim 6
wherein at least one of the irradiance, the pulse frequency and the pulse width of the coagulation pulses is settable.

8. A pulsed light source as claimed in claim 1, wherein the ablation radiation is laser radiation with a wavelength in the infrared range.

9. A pulsed light source as claimed in claim 1, wherein the ablation radiation is the light of a pulsed high-pressure gas-discharge lamp or laser diode.

10. A pulsed light source as claimed in claim 1 wherein the irradiance of the coagulation radiation is constant over time.

11. A pulsed light source as claimed in claim 1,
wherein the light source is an Er:YAG laser crystal which generates by continuous excitation the coagulation radiation and by pulsed excitation the ablation pulses.

12. A pulsed light source as claimed in claim 11,
wherein a laser diode arrangement is provided for the continuous excitation of the laser crystal to generate the continuous waveform and a flash lamp is provided for the pulsed excitation of the laser crystal to generate the pulsed waveform.

13. A pulsed light source as claimed in claim 1, wherein the irradiance of the coagulation radiation changes over time.

14. A pulsed light source as claimed in claim 13, wherein the irradiance of the coagulation radiation decreases steadily over time.

15. A pulsed light source as claimed in claim 13, wherein the continuous waveform changes periodically between one of a zigzag waveform and a sawtooth waveform.

16. A pulsed light source as claimed in claim 1, wherein the light means generate the coagulation radiation in the form of coagulation pulses with a particular pulse frequency.

17. A pulsed light source as claimed in claim 16, wherein the pulse frequency of the coagulation pulses is higher than the pulse frequency of the ablation pulses.

18. A pulsed light source as claimed in claim 16, wherein the coagulation pulses overlap at least in part the ablation pulses.

* * * * *